(12) United States Patent
Okhmatovski

(10) Patent No.: US 8,933,837 B2
(45) Date of Patent: Jan. 13, 2015

(54) IMAGING SYSTEM AND METHOD USING SPATIALLY SEPARATED RADIATED FIELDS

(75) Inventor: Vladimir Okhmatovski, St. Clements (CA)

(73) Assignee: Univeristy of Manitoba, Winnipeg, Manitoba (CA)

( * ) Notice: Subject to any disclaimer, the term of this patent is extended or adjusted under 35 U.S.C. 154(b) by 440 days.

(21) Appl. No.: 13/381,525

(22) PCT Filed: Jun. 25, 2010

(86) PCT No.: PCT/US2010/039936
§ 371 (c)(1),
(2), (4) Date: Mar. 23, 2012

(87) PCT Pub. No.: WO2011/002674
PCT Pub. Date: Jan. 6, 2011

(65) Prior Publication Data
US 2012/0168607 A1 Jul. 5, 2012

Related U.S. Application Data

(60) Provisional application No. 61/222,821, filed on Jul. 2, 2009.

(51) Int. Cl.
*G01S 13/00* (2006.01)
*G01S 13/89* (2006.01)
*A61B 5/05* (2006.01)

(52) U.S. Cl.
CPC .............. *G01S 13/89* (2013.01); *A61B 5/0507* (2013.01); *A61B 5/05* (2013.01)
USPC ......................................................... 342/195

(58) Field of Classification Search
CPC ........................................................ G01S 13/89
USPC ..................................................... 342/22, 195
See application file for complete search history.

(56) References Cited

U.S. PATENT DOCUMENTS

| 5,252,922 | A | * | 10/1993 | Larson, III ................... 324/309 |
| 5,588,032 | A | | 12/1996 | Johnson et al. |
| 6,448,788 | B1 | | 9/2002 | Meaney et al. |
| 6,570,955 | B1 | * | 5/2003 | Siffert et al. .................... 378/54 |
| 7,280,068 | B2 | | 10/2007 | Lee et al. |
| 7,283,085 | B2 | | 10/2007 | Lee et al. |
| 7,298,318 | B2 | | 11/2007 | Baharav et al. |
| 7,327,304 | B2 | | 2/2008 | Baharav et al. |

(Continued)

FOREIGN PATENT DOCUMENTS

GB 2 422 261 8/2007

OTHER PUBLICATIONS

International Search Report and Written Opinion issued Jan. 26, 2011, in the Republic of Korea, Patent Application No. PCT/US2010/039936, filed Jun. 25, 2010, 6 pages.

(Continued)

*Primary Examiner* — Timothy A Brainard
(74) *Attorney, Agent, or Firm* — Mueting, Raasch & Gebhardt, P.A.

(57) ABSTRACT

Methods and systems for use in imaging an imaging domain that spatially separate a scattered field and reconstruct an image based on the spatially separated scattered field (e.g., for use in microwave imaging applications including tumor detection in human tissue, etc.).

26 Claims, 9 Drawing Sheets

(56) References Cited

U.S. PATENT DOCUMENTS

| | | | |
|---|---|---|---|
| 7,333,055 | B2 | 2/2008 | Baharav et al. |
| 7,504,993 | B2 | 3/2009 | Young et al. |
| 2003/0184757 | A1 | 10/2003 | Bevilacqua et al. |
| 2005/0277835 | A1 | 12/2005 | Angelsen et al. |
| 2009/0015842 | A1 | 1/2009 | Leitgeb et al. |
| 2009/0028433 | A1* | 1/2009 | Tolliver et al. ............... 382/173 |
| 2009/0131921 | A1 | 5/2009 | Kurtz et al. |

OTHER PUBLICATIONS

International Preliminary Report on Patentability issued Jan. 26, 2011, in the Republic of Korea, Patent Application No. PCT/US2010/039936, filed Jun. 25, 2010, 4 pages.

Caorsi et al. "A computational technique based on a real-coded genetic algorithm for mircrowave imaging purposes", *IEEE Trans. Geosci. Remote Sensing*, 2000, vol. 38, No. 4, pp. 1697-1708.

Chew et al., "Reconstruction of two-dimensional permittivity distribution using the distorted Born interative method", *IEEE Trans. Med. Imaging*, 1990, vol. 9, No. 2, pp. 218-225.

Jin et al. "Time Reversal Beamforming for Microwave Breast Cancer Detection", ICIP 2007, *IEEE, Conference Publications*, Sep. 16, 2007-Oct. 19, 2007, vol. 5, pp. 13-16.

Kleinman et al., "A modified gradient method for two-dimensional problem in tomography", *J. Comput. Appli. Math.*, 1992, vol. 42, No. 1, pp. 17-35.

Rubaek et al., "Nonlinear microwave imaging for breast-cancer screening using Gauss-Newton's method and the CGLS inversion algorithm", *IEEE Trans. Antennas and Propragation*, Aug. 2007, vol. 55, No. 8, pp. 2320-2331.

Van Den Berg et al., "A contrast source inversion method", *Inverse Problems—IOP Publishing*, 1997, vol. 13, pp. 1607-1620.

Varslot et al., "Wide-band pulse echo imaging with distributed apertures in multi-path environments", *Inverse Problems—IOP Publishing*, Jun. 30, 2008, vol. 24, pp. 1-28.

Veselago, "The electrodynamics of substances with simultaneously negative values of $\varrho$ and $\mu$", *Sov. Phys. Usp.*, 1968, vol. 10, pp. 509-514.

* cited by examiner

PARABOLIC MIRRORS: RECONSTRUCTED IMAGE VS. TRUE CONTRAST

| $\chi$ | True $\chi$ | | $\chi$ with focusing | | $\chi$ without focusing | |
|---|---|---|---|---|---|---|
| | $\Re\chi$ | $\Im\chi$ | $\Re\chi$ | $\Im\chi$ | $\Re\chi$ | $\Im\chi$ |
| $S_1$ | 0.0 | 0.00 | 0.00002 | 0.00001 | -0.01 | 0.01 |
| $S_2$ | 0.0 | 0.00 | 0.00002 | 0.00006 | 0.02 | -0.13 |
| $S_3$ | 4.0 | -0.03 | 3.99646 | -0.03144 | 0.18 | 0.03 |
| $S_4$ | 4.0 | -0.03 | 3.99509 | -0.02146 | -0.67 | 0.84 |
| $S_5$ | 9.0 | -1.00 | 8.91618 | -1.00660 | -0.43 | 0.29 |
| $S_6$ | 9.0 | -1.00 | 8.96508 | -1.07124 | -0.19 | 1.03 |
| $S_7$ | 9.0 | -1.00 | 9.00962 | -1.05255 | -0.16 | -0.07 |
| $S_8$ | 4.0 | -0.03 | 4.00395 | -0.03674 | -1.15 | 1.63 |
| $S_9$ | 4.0 | -0.03 | 3.99959 | -0.03667 | 0.95 | -0.07 |
| $S_{10}$ | 0.0 | 0.00 | 0.00003 | -0.00004 | 0.00 | -0.07 |
| $S_{11}$ | 0.0 | 0.00 | -0.00004 | 0.00001 | 0.00 | 0.01 |

*Fig.* 7

IMAGING SYSTEM AND METHOD USING SPATIALLY SEPARATED RADIATED FIELDS

CROSS-REFERENCE TO RELATED APPLICATIONS

This application is the §371 U.S. National Stage of International Application No. PCT/US2010/039936, filed 25 Jun. 2010, which claims the benefit of U.S. Provisional Patent Application Ser. No. 61/222,812 filed 2 Jul. 2009, entitled "Imaging System and Method Using Spatially Separated Radiated Fields," each of which are incorporated herein by reference in their entireties.

TECHNICAL FIELD

The present invention relates generally to imaging. More particularly, the present invention pertains to the use of methods and systems for use in imaging applications (e.g., such as microwave imaging applications).

Microwave imaging has numerous practical applications ranging from tumor detection in human tissues to underground location of the oil and gas deposits. Despite its practical importance, microwave imaging problems remain with substantial difficulties encountered when it comes to achieving millimeter-sized resolution or dealing with high contrast objects. The primary difficulty in constructing effective imaging algorithms may stem from the non-linearity of the associated inverse scattering problem and the ill-posedness of the pertinent integral equation formulation.

Two classes of methodologies that have been partially successful in solving the inverse problem are methods minimizing the error in the scattered field outside the imaging domain through repetitive solution of the forward problem (see, e.g., W. C. Chew and Y. M. Wang, "Reconstruction of two-dimensional permittivity distribution using the distorted Born iterative method," IEEE Trans. Med. Imaging, vol. 9, no. 2, pp. 218-225, 1990; T. Rubaek, et. al., "Nonlinear microwave imaging for breast-cancer screening using Gauss-Newton's method and the CGLS inversion algorithm," IEEE Trans. Antennas and Propag., vol. 55, no. 8, pp. 2320-2331, August 2007; and S. Caorsi, et. al., "A computational technique based on a real-coded genetic algorithm for microwave imaging purposes," IEEE Trans. Geosci. Remote Sensing, vol. 38, no. 4, pp. 1697-1708, 2000) and methods based on minimization of the error in both the scattered field outside the imaging domain and total field inside the imaging domain through repetitive evaluation of the near-to-far field translations (see, e.g., R. E. Kleinman and P. M. van den Berg, "A modified gradient method for two-dimensional problem in tomography," J. Comput. Appl. Math., vol. 42, no. 1, pp. 17-35, 1992; and P. M. van den Berg and R. E. Kleinman, "A contrast source inversion method," Inverse Probl., vol. 13, pp. 1607-1620, 1997). Both such approaches are iterative in nature and utilize non-directional Green's function kernels.

SUMMARY

One exemplary method for use in imaging an imaging domain disclosed herein may include providing an incident field to interrogate an image domain resulting in a scattered field emanating from the image domain and spatially separating the scattered field emanating from the image domain by directing radiated fields produced by a plurality of individualized regions of the image domain. Spatially separating the scattered field may result in a radiated field corresponding to each of the plurality of individualized regions of the image domain. The exemplary method may further include sampling the radiated fields at each of a plurality of observation locations corresponding to each of the plurality of individualized regions of the image domain and reconstructing an image corresponding to the image domain based on the sampled radiated fields.

For example, in one or more embodiments, reconstructing an image corresponding to the image domain based on the sampled radiated fields may include using a well-conditioned diagonally-dominant matrix representative of a linear system of linear equations each corresponding to one of the plurality of observation locations.

In one or more exemplary methods disclosed herein, spatially separating the scattered field may include directing at least one of or each of the radiated fields in a different direction than the other radiated fields. For example, directing at least one of or each of the radiated fields in a different direction than the other radiated fields may include directing at least one of or each of the radiated fields at a different angle than the other radiated fields.

Further, in one or more exemplary methods disclosed herein, spatially separating the scattered field may include directing at least one of or each of the radiated fields to a different observation location of the plurality of observation locations than the other observation locations of the plurality of observation locations at which the other radiated fields are directed. Further, each of the plurality of observation locations may be located a distance away from other observation locations of the plurality of observation locations.

Still further, in one or more exemplary methods disclosed herein, spatially separating the scattered field emanating from the image domain may include using separation apparatus to direct the radiated fields produced by the plurality of individualized regions of the image domain. For example, the separation apparatus may include a Veselago lens, a phased-antenna array, and/or a parabolic mirror.

Yet still further, in one or more exemplary methods disclosed herein, the plurality of observation locations may correspond to a plurality of focal points, and the exemplary methods may further include focusing each of the radiated fields at one of the plurality of focal points.

One exemplary system for use in imaging an imaging domain disclosed herein includes a transmitting source, separation apparatus, receiving apparatus, and processing apparatus. The transmitting source may be configured to provide an incident field. The incident field, when interrogating an image domain, results in a scattered field emanating from the image domain.

The separation apparatus of the exemplary systems described herein may be configured to spatially separate a scattered field emanating from the image domain upon being interrogated by the incident field by directing radiated fields produced by a plurality of individualized regions of the image domain resulting in a radiated field corresponding to each of the plurality of individualized regions of the image domain.

In one or more exemplary systems described herein, the separation apparatus may be further configured to direct at least one of or each of the radiated fields in a different direction than the other radiated fields. For example, at least one of or each of the radiated fields directed by the separation apparatus may be directed at a different angle than the other radiated fields.

Further, in one or more exemplary systems described herein, the separation apparatus may be further configured to direct at least one of or each of the radiated fields to a different observation location of the plurality of observation locations than other observation locations of the plurality of observation locations at which the other radiated fields are directed. Further, each of the plurality of observation locations may be located a distance away from the other observation locations of the plurality of observation locations.

Still further, in one or more exemplary systems described herein, the separation apparatus may include a Veselago lens, a parabolic mirror, and/or a phased-antenna array.

The receiving apparatus of the exemplary systems described herein may be configured to receive the radiated fields at each of a plurality of observation locations corresponding to each of the plurality of individualized regions of the image domain. Further, the plurality of observation locations may correspond to a plurality of focal points, and in one or more embodiments, the exemplary separation apparatus may include focusing apparatus configured to focus each radiated field at a different focal point of the plurality of focal points than other focal points of the plurality of focal points at which the other radiated fields are focused. In one or more exemplary systems described herein, the focusing apparatus may include a parabolic mirror for each radiated field.

The processing apparatus of the exemplary systems described herein may be configured to reconstruct an image corresponding to the image domain based on the received radiated fields. For example, the processing apparatus may be operable to reconstruct an image corresponding to the image domain based on the received radiated fields using a well-conditioned diagonally-dominant matrix representative of a linear system of linear equations each corresponding to one of the plurality of observation locations.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 6 depicts a table including data representative of an image domain and reconstruction of an image domain using the imaging configuration of FIG. 3.

DETAILED DESCRIPTION OF EXEMPLARY EMBODIMENTS

Figure 1:
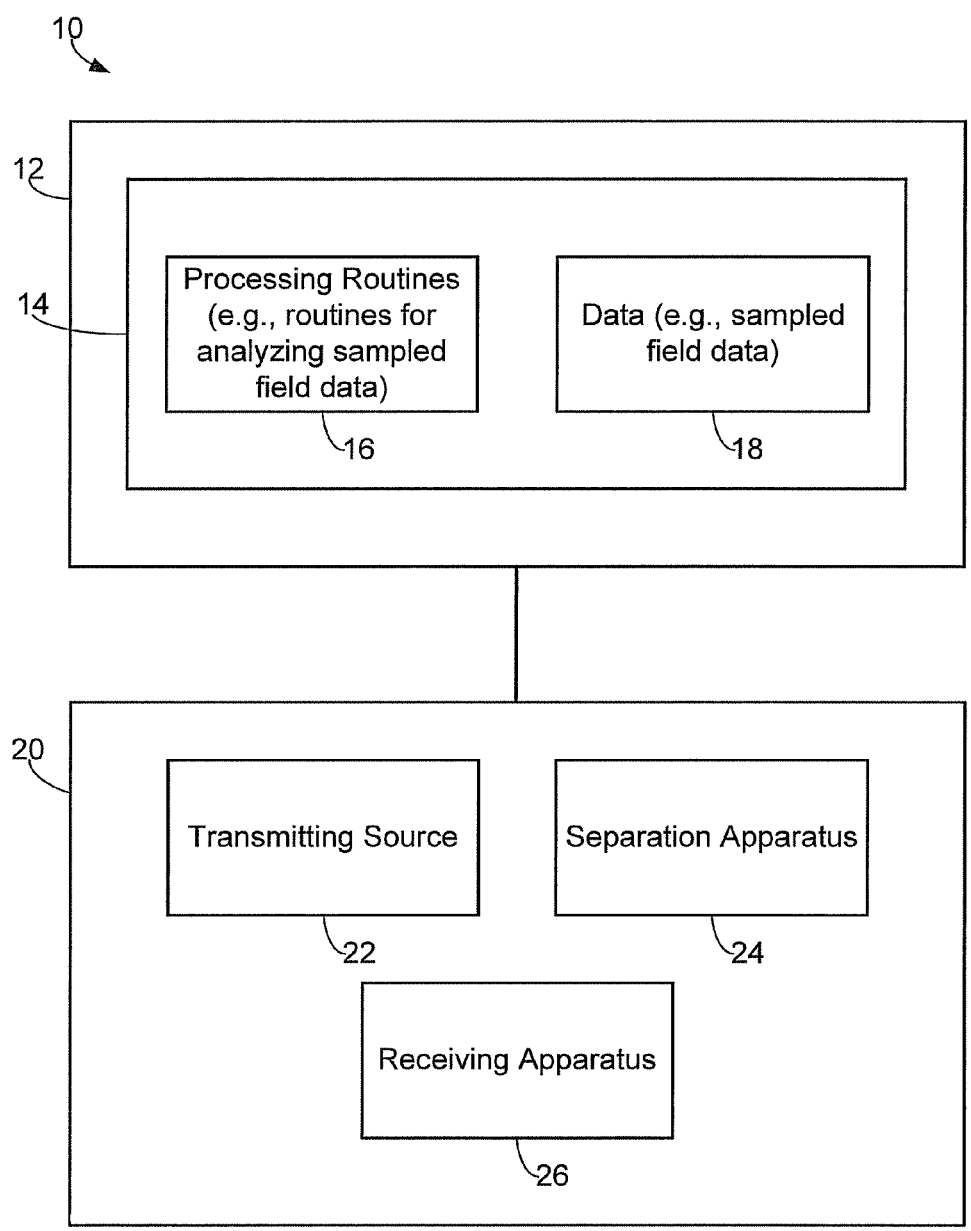
FIG. 1 depicts an exemplary imaging system including a processing apparatus and an imaging configuration.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods and systems shall be described with reference to FIGS. 1-9. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timing, one or more shapes and/or sizes, or types of elements, may be advantageous over others.

The systems and methods described herein differ from conventional imaging approaches where the total field produced by all the regions of the contrast sources is collected at a given set of the observation points. Instead, one or more embodiments of the systems and methods described herein spatially separate (or decouple) the radiated fields produced by the individual regions (basis functions) of the contrast sources. Such separation of the scattered fields emanating from the basis functions of the discretized imaging region may be achieved by using an imaging configuration that provides a medium with a specific Green's function behavior. In particular, the Green's function may, e.g., feature a singular or focal field behavior at one or more points sufficiently separated from the source point.

For example, one example of such a medium is a set of parabolic mirrors as shown in and described with reference to FIG. 3. In this example, in addition to the singularity of the field at the source location in the focal plane of the source mirror, a high concentration of the field may be observed at the focus of corresponding receiving mirrors due to the transmitting beam steering as the source point shifts off the focus.

Another example of a medium featuring spatial separation desired properties is a Veselago lens as shown in and described with reference to FIG. 7 (see, e.g., V. G. Veselago, "The electrodynamics of substances with simultaneously negative values of Q and µ," Sov. Phys. Usp., vol. 10, pp. 509-514, 1968), which can create ideally singular or highly concentrated fields at particular focal points depending on its material properties. Upon availability of such Green's function, the discretized inverse problem can be made well-conditioned and solved through a direct matrix inversion.

FIG. 1 shows an imaging system 10 including a processing apparatus (block 12) and data storage (block 14). Further, imaging system 10 includes imaging configuration (block 20), e.g., controllable or selectable components used to provide data (e.g., microwave imaging data). As further described herein, the imaging configuration (block 20) may be any suitable configuration and use any suitable components to provide an incident field to interrogate an image domain (e.g., an object in a region, a portion of an object in a region, etc.) resulting in a scattered field, to spatially separate the scattered field, and to sample spatially separated radiated fields (e.g., resulting from the spatial separation of the scattered field).

As shown, the imaging configuration (block 20) includes a transmitting source (block 22), separation apparatus (block 24), and receiving apparatus (block 26). The transmitting source (block 22) may include one or more antennas or any one or more devices capable of delivering energy (e.g., electromagnetic energy generated at a frequency in the range of about 0.3 GHz to about 20 GHz) to irradiate or interrogate an image domain resulting in a scattered field emanating from the image domain. Further, the transmitting source (block 22) may include one or more movable or non-movable point sources. Still further, the transmitting source (block 22) may include directional or multidirectional devices. In at least one embodiment, the transmitting source (block 22) may include multiple devices capable of delivering energy at various intensities to, e.g., illuminate some portions of the image domain differently than others. Further, in at least one embodiment, the transmitting source (block 22) includes a single omnidirectional antenna delivering electromagnetic energy at a frequency that, e.g., enables the separation apparatus (block 24) to provide spatial separation of the scattered field to achieve a desired imaging quality. The electromagnetic energy may also be delivered to the object in the form of at least one directed beam provided by a directional antenna (e.g., one or a plurality beams provided by one or more antennas).

The separation apparatus (block 24) may include one or more devices capable of spatially separating a scattered field (e.g., the scattered field produced by the transmitting source (block 22) interrogating an image domain, or in other words, the scattered field produced by the image domain in response to interrogation by the transmitting source (block 22)) by directing radiated fields produced by a plurality of individualized regions of an image domain. An individualized region of an image domain may be defined as including at least a primary portion and additional portions, e.g., the portions adjacent the primary portion. The radiated field emanating from the individualized region (i.e., the portion of the scattered field corresponding to the individualized region), however, primarily emanates from the primary portion of the individualized region. In other words, although radiated fields may emanate from portions of the image domain adjacent the primary portion of the individualized region, the majority of the radiated field corresponding to the particular individualized region emanates from the primary portion of the individualized region. As such, the majority of the radiated field emanating from the individualized region is representative of the primary portion of the individualized region. In at least one embodiment, each individualized region may be represented by a pixel or a group of pixels (e.g., pixels adjacent one another) in a reconstructed image (e.g., an image reconstructed based on the radiated field data obtained using imaging system 10).

In one or more embodiments, at least a part of the non-primary portions, or additional portions, of an individualized region may overlap with an adjacent individualized portion. However, since the majority of the radiated field emanating from the individualized region is representative of the primary portion of the individualized region, the individualized region may be described as being non-overlapping, or discrete, from adjacent individualized regions (e.g., the primary portion of each individualized region may not overlap with another primary portion of the other individualized regions).

The spatial separation of the scattered field using the separation apparatus (block 24) results in a radiated field corresponding to each of the plurality of individualized regions. In other words, the separation apparatus (block 24) spatially separates the scattered field such that each radiated field associated with an individualized region of an image domain may be directed in a way such that each radiated field can be sampled or collected, e.g., at one or more of a plurality of particular observation points.

Further, at least in one embodiment, each of the observation points may be separated a distance apart from on another. Spatially separating the scattered field may include directing one or more of the radiated fields to one of the plurality of observation locations (e.g., where each of the plurality of observation locations is located separately from the other observation locations). As such, each of the radiated fields may be directed to an observation location located at a distance from the other observation locations to which the other radiated fields are directed. In other words, each (or at least one) of the radiated fields that are directed by the separation apparatus (block 24) may be spatially separated by a distance at least where the radiated fields are sampled or collected at the plurality of observation locations.

The separation apparatus (block 24) may spatially separate the scattered field using one or more techniques. In at least one embodiment, the separation apparatus (block 24) may direct at least one or each radiated field (e.g., each radiated field corresponding to an individualized region of the image domain) in a particular direction such that each radiated field may be collected or sampled using receiving apparatus (block 26) (e.g., receiving apparatus located along such a particular direction). In other words, the separation apparatus (block 24) may spatially separate the scattered field by directing at least one or each of the radiated fields in a different direction than the other radiated fields (e.g., directing each of the radiated fields at a different angle than the other radiated fields). As a result, each different direction and/or angle that each radiated field is directed in and/or at may correspond to an individualized region of the image domain.

Figure 3:
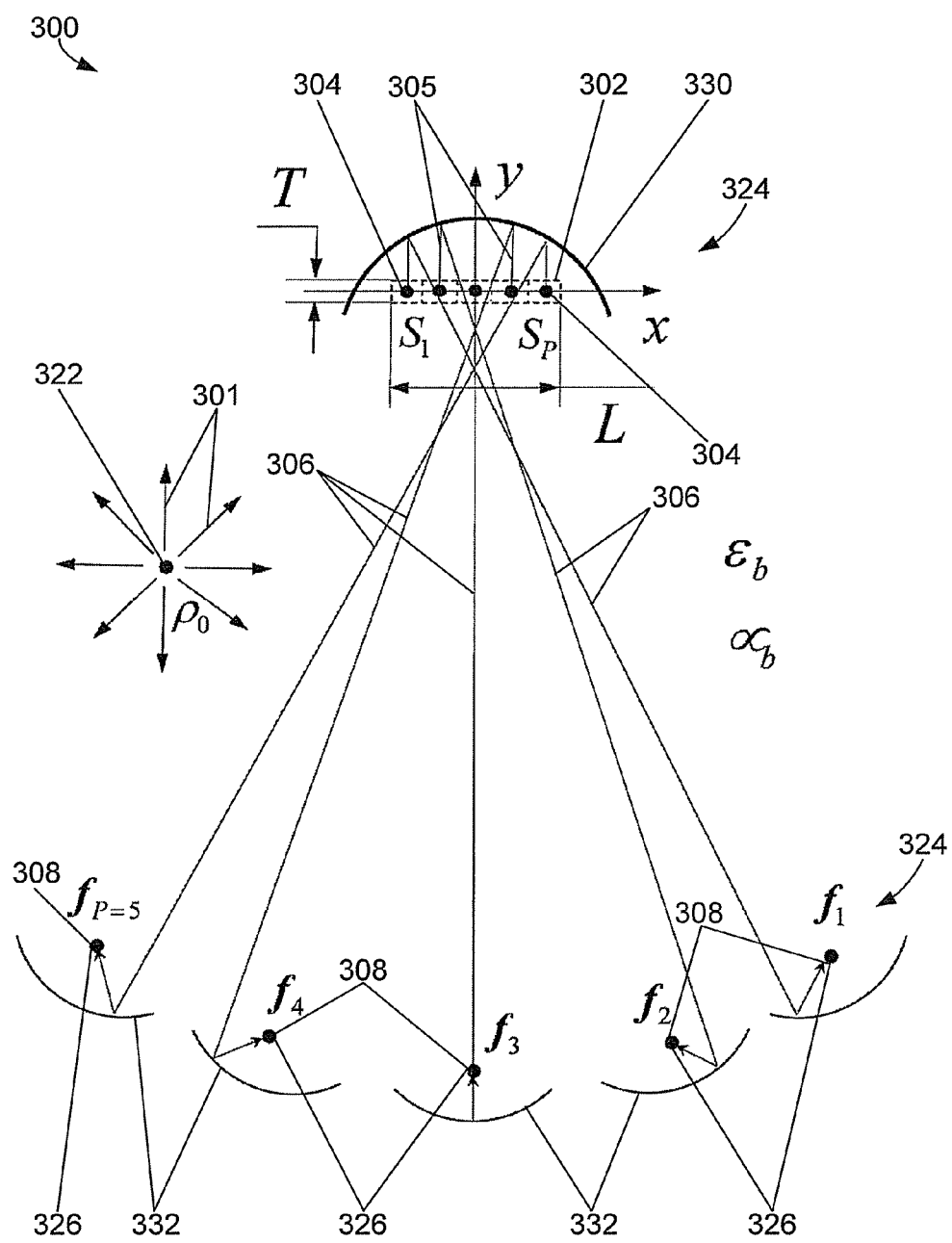
FIG. 3 depicts an exemplary imaging configuration using a parabolic mirror.
Figure 9:
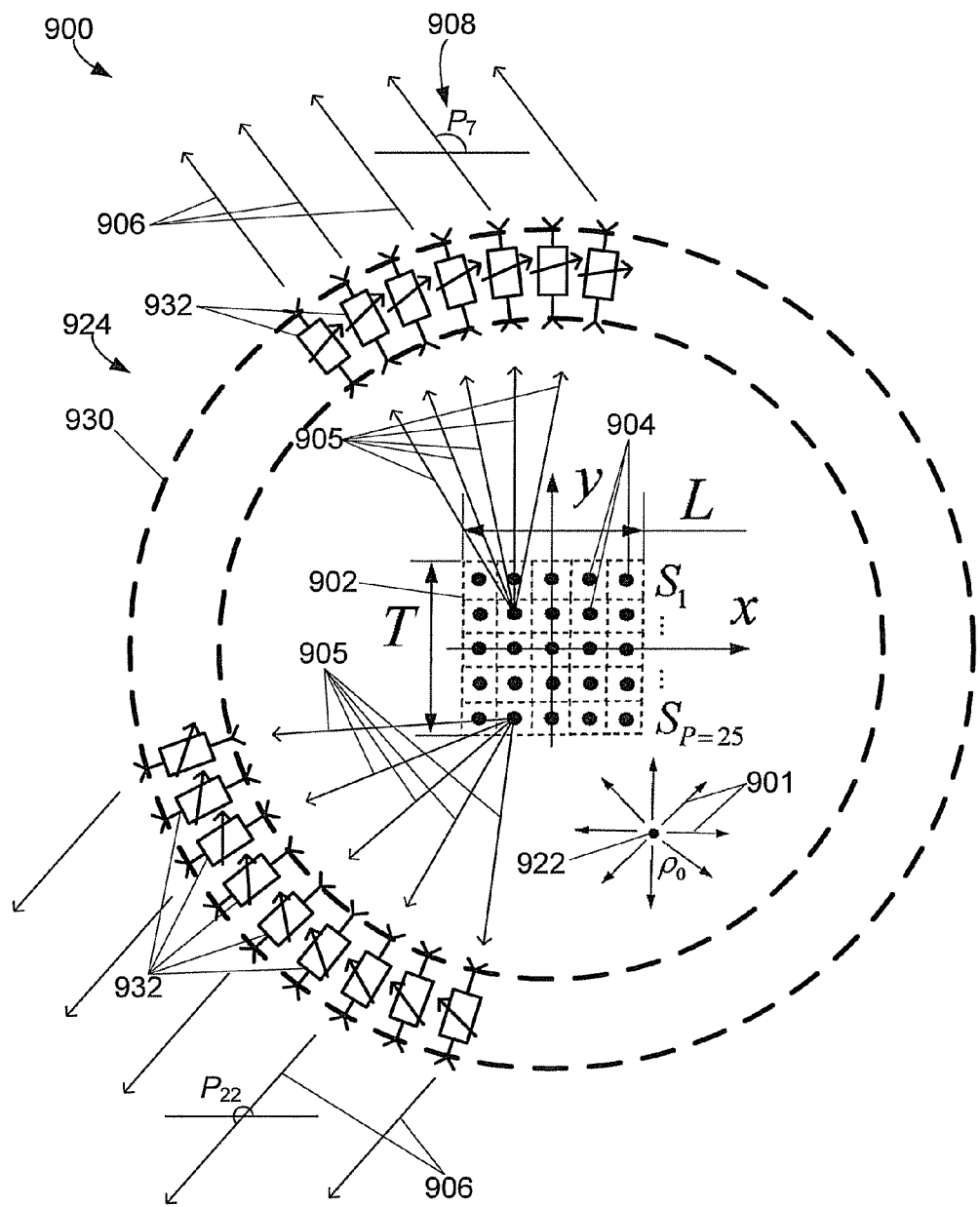
FIG. 9 depicts an exemplary imaging configuration using a phased-antenna array.

For example, the parabolic mirror imaging configuration described herein with reference to FIG. 3 and the phased-antenna array imaging configuration described herein with reference to FIG. 9 directs each radiated field at a particular direction and at a particular angle.

In at least another embodiment, the separation apparatus (block 24) may direct each radiated field to a particular focal point (e.g., each focal point being separated by a distance) such that each radiated field may be collected using receiving apparatus (block 26) configured to collect each radiated field at each of the particular focal points. For example, the Veselago lens imaging configuration described herein with reference to FIG. 7 directs each radiated field to a particular focal point. Further, for example, the imaging configuration described herein with reference to FIG. 3 uses focusing apparatus (e.g., a plurality of parabolic mirrors) to focus each radiated field to a particular focal point.

The receiving apparatus (block 26) may include one or more devices (e.g., antennas, mirrors, etc.) capable of receiving the radiated fields directed using the separation apparatus (block 24). The configuration of the receiving apparatus (block 26) and/or the devices includes therein may depend on how the separation apparatus (block 24) directs each radiated field.

For example, the separation apparatus (block 24) may direct each radiated field in a particular direction and optionally focus each radiated field to a particular observation location (or focal point). In at least one embodiment, the receiving apparatus (block 26) includes an antenna for each particular direction and/or each particular observation location. For example, the parabolic mirror imaging configuration described herein with reference to FIG. 3 uses separation apparatus including a parabolic mirror to spatially separate the scattered field resulting in radiated fields separated by direction and a parabolic mirror for each particular direction to collect and focus each directed radiated field at each observation location (e.g., each observation location located at a particular focal point). The receiving apparatus includes an antenna at each observation location to receive each radiated field.

In other words, the separation apparatus (block 24) may direct at least one of or each of the radiated fields to a different observation location of the plurality of observation locations than the other observation locations of the plurality of observation locations at which the other radiated fields are directed.

In at least another embodiment, the receiving apparatus (block 26) includes fewer antennas than the number of particular directions (at which the radiated fields are directed) and/or particular observation locations. For example, the receiving apparatus (block 26) may include one or more positionable/movable antennas or devices that may be positioned or moved into each of the observation locations to receive each radiated field.

Figure 7:
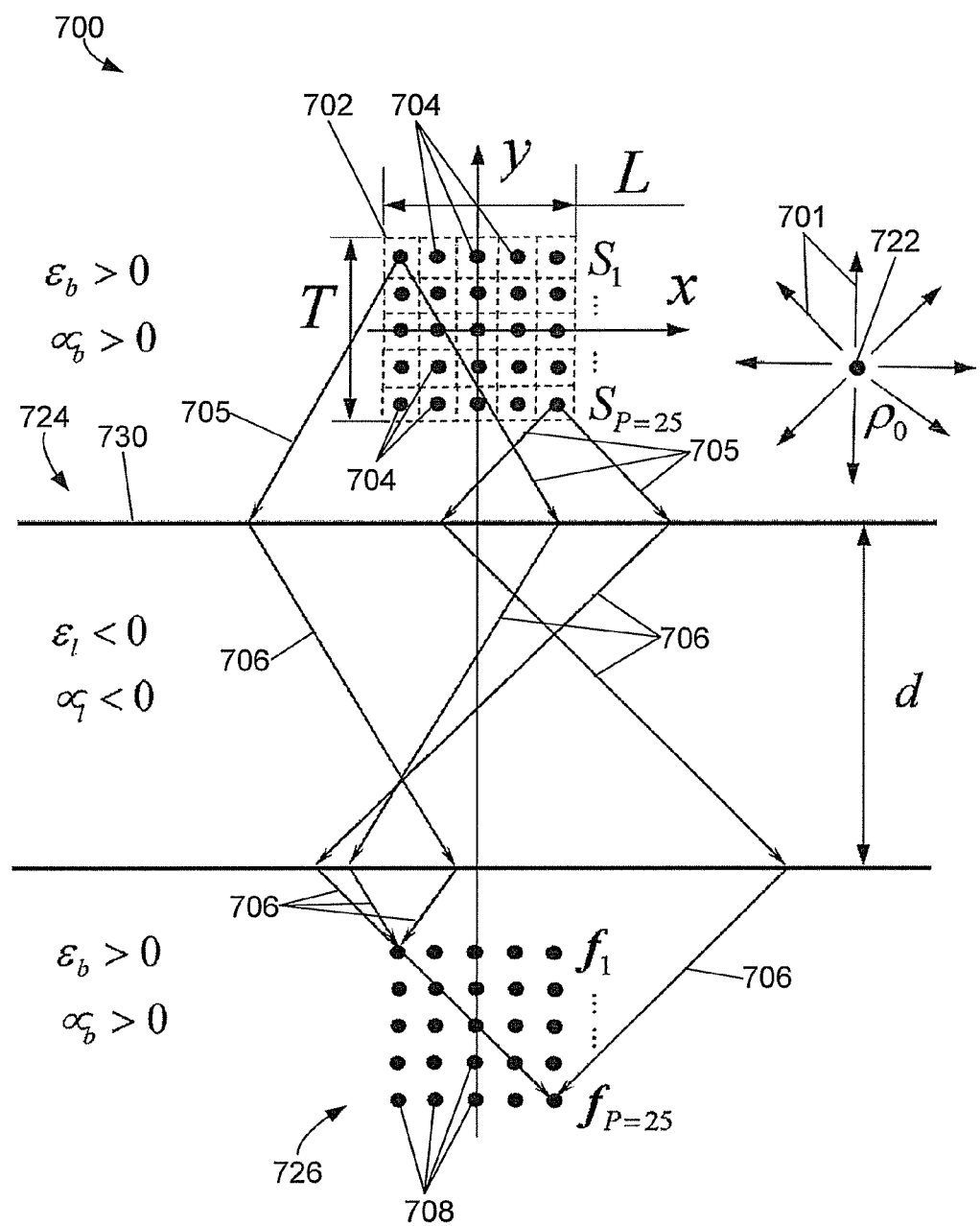
FIG. 7 depicts an exemplary imaging configuration using a Veselago lens.

Further, for example, the Veselago lens imaging configuration described herein with reference to FIG. 7 uses a Veselago lens to spatially separate the scattered field resulting in radiated fields and to focus each radiated field at each observation location (e.g., each observation location located at a particular focal point). The receiving apparatus as depicted in the Veselago lens imaging configuration of FIG. 7 includes an antenna positioned at each observation location to receive each radiated field.

In at least one embodiment, the receiving apparatus may include a dipole antenna located at each observation location or a dipole antenna movable/positionable to each or many of the observation locations. The dipole antenna may be configured to receive a particular component (e.g., x-, y-, or z-component) of the vector electric field at the observation locations.

In at least another embodiment, the receiving apparatus may include a composition of three orthogonal dipole antennas simultaneously receiving all three components of the vector electric field at a particular observation location. The received radiated fields may be measured at one observation location at a time (e.g., iteratively using movable antennas) or multiple observation locations at a time depending on the type of the field measurement system utilized (e.g., a near-field scanner, etc.).

Further, although not depicted, the system 10 may include additional detectors, sensors, transmitting, and/or receiving components used for collection of scattered field data, e.g., including any suitable components such as transmitting antennas (e.g., antenna arrays), receiving antennas (e.g., antenna arrays), or any other apparatus (e.g., microwave imaging apparatus) contemplated to be used in combination with processing apparatus (block 12) of the system 10.

The processing apparatus (block 12), may be, for example, any fixed or mobile computer system (e.g., a personal computer or mini computer). The exact configuration of the computing apparatus is not limiting and essentially any device capable of providing suitable computing capabilities and control capabilities (e.g., control the imaging set up configuration and acquire data, such as scattered field information) may be used. Further, various peripheral devices, such as a computer display, mouse, keyboard, memory, printer, scanner, are contemplated to be used in combination with processing apparatus (block 12) of the data storage (block 14).

Figure 2:
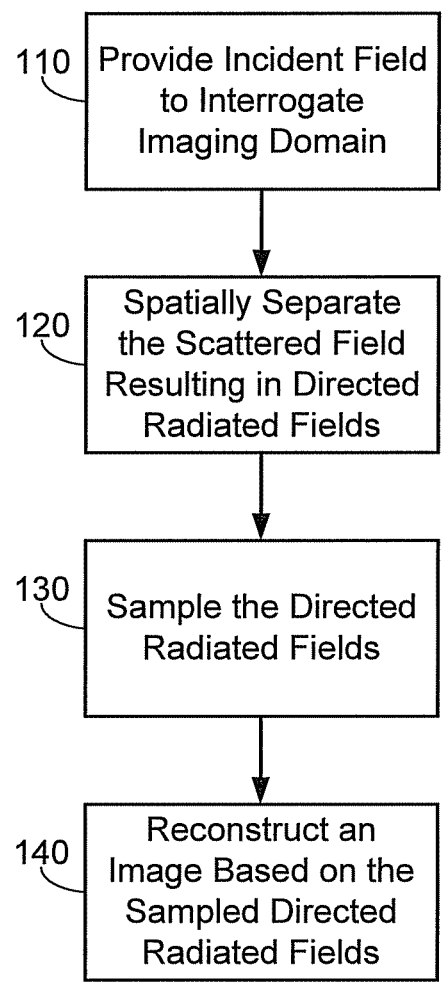
FIG. 2 depicts a general block diagram of an exemplary imaging method for imaging an imaging domain.

Data storage (block 14) allows for access to processing programs or routines (block 16) and one or more other types of data (block 18) that may be employed to carry out the illustrative imaging methods, e.g., as shown generally in the block diagram of FIG. 2.

The methods and systems described herein may include one or more processes or programs (or systems including such programs). For example, the systems and methods described herein may be considered to include multiple processes or programs that may be implemented alone or in combination. Further, the output of one program or process may be used as an input by another program described herein or any other program that may operate on the input, the input to the process described herein may be received from an output of another process, or the multiple processes may be used in any other effective combination.

For example, processing programs or routines (block 16) may include programs or routines for performing matrix mathematics, compression algorithms, standardization algorithms, comparison algorithms, vector mathematics, or any other processing required to implement one or more embodiments of the exemplary methods described herein. Data (block 18) may include, for example, spatially separated scattered field data (e.g., radiated field data representative of a scattered field emanating from an image domain), data representative of measurements, results from one or more processing programs or routines employed according to the present disclosure, or any other data that may be necessary for carrying out the one or more processes described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or processes as described herein or as would be applied in a known fashion.

The program used to implement the methods described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein.

Likewise, the imaging system 10 may be configured at a remote site (e.g., an application server) that allows access by one or more users via a remote computer apparatus (e.g., via a web browser), and allows a user to employ the functionality according to the present invention (e.g., user accesses a graphical user interface associated with one or more programs to process data).

Further, in one or more embodiments, the output (e.g., an image, image data, an image data file, a digital file, a file in user-readable format, etc.) may be analyzed by a user, used by another machine that provides output based thereon, etc.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by processing apparatus (block 12) described herein.

Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

FIG. 2 shows a general block diagram of an exemplary imaging method 100 for imaging one or more regions or imaging domains. One will recognize that one or more of the blocks of functionality described therein may be carried out using one or more programs or routines, and/or any other components of an imaging system, e.g., imaging system 10.

Generally, the method 100 includes providing an incident field (e.g., a field generated by a microwave source such as at a frequency in the range of 0.3 GHz to 1000 GHz) to interrogate, irradiate, or illuminate an image domain (or portion of an image domain) resulting in a scattered field emanating from the image domain (block 110) (e.g., an image domain or portion thereof being imaged). As described herein, the incident field may be provided by transmitting source (block 22), which may include one or more devices capable of delivering electromagnetic energy.

The scattered field emanating from the image domain is spatially separated by directing radiated fields produced by a plurality of individualized regions of the image domain (block 120). Spatially separating the scattered field results in a radiated field corresponding to each of the plurality of individualized regions. As described herein, each radiated field may be directed in a particular direction (e.g., directed at a particular angle) and/or focused to a particular observation location (e.g., a focal point).

Each of the directed radiated fields is sampled (block 130) at each of a plurality of observation locations to provide data to reconstruct an image. As described herein, each of the directed radiated fields may be sampled (e.g., measured) using one or more antennas either fixed at or movable into each of the plurality of observation locations. Each of the plurality of observation locations corresponds to each of the plurality of individualized regions of the image domain. As described herein, the apparatus and/or techniques to sample each radiated field may depend on the type of separation apparatus (block 24) used in the imaging configuration.

An image representative of the image domain or a portion thereof may be reconstructed based on the sampled radiated fields (block 140). More specific description of one or more embodiments of image reconstruction is described herein with reference to FIGS. 3-8.

Further, in one or more embodiments, reconstructing an image corresponding to the image domain based on the sampled radiated fields may include using a well-conditioned diagonally-dominant matrix representative of a linear system of linear equations each corresponding to one of the plurality of observation locations.

Generally, the methods and systems as described herein may utilize algorithms implementing matrix mathematics (e.g., matrix inversions, substitutions, etc.) to reconstruct the images described herein (e.g., from sampled field data). In view of the above, it will be readily apparent that the functionality as described in one or more embodiments may be implemented in any manner as would be known to one skilled in the art. As such, the computer language, the computer system, or any other software/hardware which is to be used to implement the present methods and/or systems shall not be limiting on the scope of the systems, processes or programs (e.g., the functionality provided by such systems, processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information.

More specific description regarding the algorithms used by the exemplary methods and systems described herein will be described. For example, the spatial separation (or decoupling) of the scattered field emanating from an image domain can be achieved through a specially constructed Green's function (i.e., a medium realizing such a Green's function). The Green's function (i.e., the medium provided, e.g., by the systems and methods described herein) may be used to form separated beams of the radiated fields produced by the distinct pixels of contrast sources as they are interrogated by an incident (or extraneous) field.

Before discussion of the exemplary image reconstruction algorithms for use within the exemplary imaging configurations, the statement of the inverse problem will be described. For example, the solution of two-dimensional (2D) time-harmonic Maxwell equations with $TM_z$-polarized field is equivalent to solving the following integral equation:

$$E(\rho) = \int_S (k^2(\rho') - k_b^2(\rho'))E(\rho')G(\rho, \rho')ds' + E^i(\rho), \quad (1)$$

where points $\rho$ are in observation domain D, $E(\rho)$ is the z-component of the total electric field $E=\hat{z}E$, $E^i(\rho)$ is the z-component of the incident field, $k(\rho)=k_0\sqrt{\in(\rho)\mu(\rho)}$ is position dependent wavenumber due to inhomogeneous spatial distribution of permittivity $\in(\rho)$ and permeability $\mu(\rho)$, $\omega$ is the cyclic frequency of the time-harmonic field, $k_0=\omega\sqrt{\in_0\mu_0}$ is the wavenumber of free space, $\in_0$ and $\mu_0$ are permittivity and permeability of free space, respectively. In equation (1) and throughout the text the $e^{i\omega t}$ time variation of the fields is assumed and suppressed, $i=\sqrt{-1}$ being the imaginary unity. Kernel $G(\rho,\rho')$ in equation (1) is the Green's function of the medium with wavenumber $k_b(\rho)=k_0\sqrt{\in_b(\rho)\mu_b(\rho)}$ in which the imaging experiment is staged. In subsequent derivations, the contrast function $\chi(\rho)=[k^2(\rho)-k_b^2(\rho)]/k_0^2$ is utilized for convenience.

Expansion of the contrast source function $W(\rho)=\chi(\rho)E(\rho)$ over $p=1, \ldots, P$ piece-wise basis functions $b_p(\rho)$ is shown below in equation (2):

$$W(\rho) = \chi(\rho)E(\rho) \cong \sum_{p=1}^{P} \chi_p E_p b_p(\rho) = \sum_{p=1}^{P} W_p b_p(\rho), \quad (2)$$

where $b_p(\rho)$ is equal to 1 when $\rho$ is in $\rho$-th pixel area $S_p$ and zero otherwise, yields a discretized form of integral equation (1) as shown below in equation (3):

$$E(\rho) - E^i(\rho) = k_0^2 \sum_{p'=1}^{P} \chi_{p'} E_{p'} \int_{S_{p'}} G_0(\rho, \rho')ds', \rho \in D. \quad (3)$$

In the inverse problem, the scattered field samples $E_p^s = E_p - E_p^i$ are known at a set of receiving points $\rho_p$, $p=1, \ldots, P$, located in the data domain D which does not intersect with the imaging domain S. The coefficients $\chi_{p'}$ and $E_{p'}$ are considered unknown. Most common approaches to the inverse problem solution treat equation (3) iteratively by either intermittently solving for unknown contrast coefficient determine $\chi_{p'}$ and imaging domain field $E_{p'}$ or through local and/or global optimization-like search for contrast source $W_{p'}$ and in-domain field coefficients $E_{p'}$. In both of such approaches, a non-directional Green's function is utilized. Usage of both such approaches with a directional Green's function medium (e.g., provided using the systems and methods described herein) separating the radiated fields may, e.g., be improved if the scattered field were separated. Since the observation points are separated from the imaging domain, the non-directional Green's function forms a smooth kernel in the discretized form of the first kind integral equation (3) which results in ill-conditioning of the inverse problem allowing only for heuristic solutions.

Next, a mathematical formulation of one non-iterative imaging algorithm used in exemplary methods and systems described herein will be described with reference to the imaging configuration depicted in FIG. 3. Both iterative imaging algorithms and other algorithms based on a least-square solution of equation (3), however, may also be utilized in the systems and methods described herein, e.g., utilizing a directional Green's function medium operable to spatially separate the scattered fields emanating from individualized regions of an image domain (e.g., an object). In other words, although a non-iterative imaging algorithm is described herein with reference to the methods and systems described herein, other imaging algorithms may also be used in the methods and systems, e.g., utilizing a directional Green's function medium, described herein.

An exemplary imaging configuration 300 using a parabolic mirror configured to image object 302 is depicted in FIG. 3. The imaging configuration 300 includes transmitting source 322, separation apparatus 324, and receiving apparatus 326.

The transmitting source 322, or source point, is configured to provide an incident field 301 to interrogate or irradiate an image domain, e.g., the object 302. The separation apparatus 324 includes a parabolic mirror 330 and focusing apparatus 332. The parabolic mirror 330 is configured (e.g., positioned in relation to the object 302) such that it may spatially separate the scattered field 305 emanating from the image domain, e.g., the object 302, by directing radiated fields 306 produced by the plurality of individualized regions 304 of the image domain (e.g., object 302). Spatially separating the scattered field 305 results in a radiated field 306 corresponding to each of the plurality of individualized regions 304.

The focusing apparatus 332 includes a plurality of parabolic mirrors positioned to focus each radiated field 306 (e.g., in a different direction) at each of the plurality of observation locations 308 corresponding to each of the plurality of individualized regions 304. Although the imaging configuration 300 as shown in FIG. 3 uses focusing apparatus 332, in one or more embodiments, such a focusing apparatus need not be used. For example, each of the radiated fields may be received at a location anywhere along the directed path, e.g., at a location along the directed path where usable data may be received.

The receiving apparatus 326 includes a plurality of antennas. Each of the plurality of antennas is located at one of the plurality of observation locations 308 and is configured to receive (e.g., such that it can be sampled) a radiated field 306 corresponding to one of the plurality of individualize regions 304.

In one or more embodiments, the receiving apparatus 326 may include fewer antennas (and parabolic mirrors for focusing) than the number of observation locations. In this configuration, the antennas (and parabolic mirrors) may be moveable to the observation locations to receive each radiated field 306 (e.g., one or more antennas moveable to the plurality of observation locations).

The algorithm to reconstruct an image using the imaging configuration 300 may be formed by constructing a well-conditioned system for contrast source function W. With respect to the Green's function $G(\rho, \rho')$ of the media being imaged in the imaging configuration 300, P individualized regions 304 located in the focal plane of the source mirror 330 and P observation points 308 placed at the focal points $f_p$ of the P receiving parabolic mirrors of the focusing apparatus 332 are considered (provided the latter are positioned to intercept the main lobe of the source mirror 330 radiation pattern as it steers due to the shift of the source point off the source mirror focus). For example, an object 302, e.g., a thin strip of dielectric material, with thickness T and length L may be located along the focal plane of the source mirror 330 as shown in FIG. 3 and interrogated with an incident field 301 of a source point 322 situated at the point $\rho_0$. Assuming that the object 302 is inhomogeneous along coordinate x and homogeneous along coordinate y, P basis functions $b_p$ are introduced to discretized the object 302 over its length L. Through placement of P observation points 308 at the focuses of the receiving mirrors of the focusing apparatus 332, the discretized integral equation (3) yields the following set of linear algebraic equations:

$$k_0^2 \sum_{p'=1}^{P} W_{p'} \int_{S_{p'}} G(f_p, \rho')ds' = E(f_p) - E^i(f_p), \quad (4)$$

where $p=1, \ldots, P$. The linear system (4) can be written in the following matrix form:

$$G \cdot W = E, \quad (5)$$

where $W=[W_1, W_2, \ldots, W_p]^\dagger$ is the vector of unknown coefficients $W_p = \chi_p E_p$ of the basis functions $b_p$ discretizing the contrast source function $W(\rho)$, $E=[E^s(f_1), E^s(f_1), \ldots, E^s(f_p)]$ is the known vector of scattered field values $E(f_p) - E^i(f_p)$ sampled at the observation points 308 of the receiving antenna (of the receiving apparatus 326) focuses $f_p$ 332. Here and elsewhere † denotes transposition. The elements of square (P×P) matrix G entering in equation (5) are given by the following expression:

$$G_{pp'} = k_0^2 \int_{S_{p'}} G(f_p, \rho')ds', \quad p, p' = 1, \ldots, P. \quad (6)$$

Thus, constructed matrix G is diagonally-dominant and well-conditioned. These properties come from a substantially higher contribution of the scattered field 305 produced at the focus (i.e., observation locations 308) of the pth receiving antenna by the pth basis function whose radiated field is formed into a beam pointing at the pth receiving antenna. At the same time, the level of scattered field 305 observed at the pth receiving antenna from all the other p'th basis functions ($p' \neq p$) is substantially smaller since the beams produced by these sources are steered away from the pth receiving antenna. The system of linear equations (5) can be solved directly or iteratively. In the case of iterative solution, the system can be solved with respect to unknown contrast source values $W_p$ or with respect to both contrast sources $W_p$ and field values $E_p$ in an optimization-like process, e.g., that searches in alternating fashion for contrast source values $W_p$ and field values $E_p$. Both direct and iterative methods of solving the inverse problem may be used with the systems and methods described herein (e.g., utilizing the Green's function medium with spatial separation properties provided by the exemplary systems and methods).

Equation (6) may be solved directly or iteratively with respect to the contrast sources values $W_p$. For example, contrast $\chi$ may be determined from contrast sources W. For that purpose, the electric field samples $E_p$, p=1, . . . , P, at the centroids $c_p$ of the elements basis function $b_p$ support elements from the known contrast source coefficients $W_p$ substituted into the following expression for the electric field equation (3) are evaluated:

$$E_p = E(c_p) = E^i(c_p) + k_0^2 \sum_{p'=1}^{P} W_{p'} \int_{S_{p'}} G(c_p, \rho') ds', \quad (7)$$

where p=1, . . . , P. Please note that P equations (7) do not form a linear system but a set of individual expressions for evaluation of total electric field values $E_p$ from previously found contrast source function samples $W_p$ for all p=1, . . . , P.

From the known values of the contrast source expansion coefficients $W_p$ and total electric field values in the imaging domain $E_p$, the desired values of contrast function coefficients $\chi_p$ are found by simple division as follows:

$$\chi_p = \frac{W_p}{E_p}, p = 1, \ldots, P. \quad (8)$$

The numerical results of the parabolic mirror imaging configuration 300 as shown in FIG. 3 are now described. In this example, the one-dimensional parabolic mirror imaging configuration 300 is considered under the time-harmonic frequency $\omega=2\pi\cdot 1.5$ GHz. The source parabolic mirror 330 may be described by the following parametric equation:

$$\rho(t)=\rho_a-at^2\hat{y}+2at\hat{x}, t\in[t_{min}, t_{max}], \quad (9)$$

taken with a=6.05 m, $t_{min}=-0.55$, $t_{max}=0.55$, and $\rho_a=a$ $\hat{y}$. At the frequency of 1.5 GHz, the length of the mirror $M=\int_{t_{min}}^{t_{max}}|\rho'(t)|dt$ is 69.816$\lambda$, where $\lambda$ is the wavelength. The mirror 330 produces the radiation pattern main lobe with a half-width $\Delta_\phi=\lambda/(2a(t_{max}-t_{min}))=0.015$ rad. The image domain subjected to image reconstruction in this example has a rectangular shape and is oriented with respect to the source parabolic mirror 330 as shown in FIG. 3 with the length L=0.9 m and thickness T=0.1 m. The true real and imaginary parts of permittivity values at the centroids of the P=11 basis function supporting elements are shown in the second and third columns of table 600 depicted in FIG. 6, respectively, while $\in_b=\in_0$ and $\mu_b=\mu=\mu_0$. The interrogating field $E^i$ as produced by source point 322 in this example is produced by a unity-strength z-directed filament of electric current located at $\rho_0=a\hat{x}$.

Figure 4:
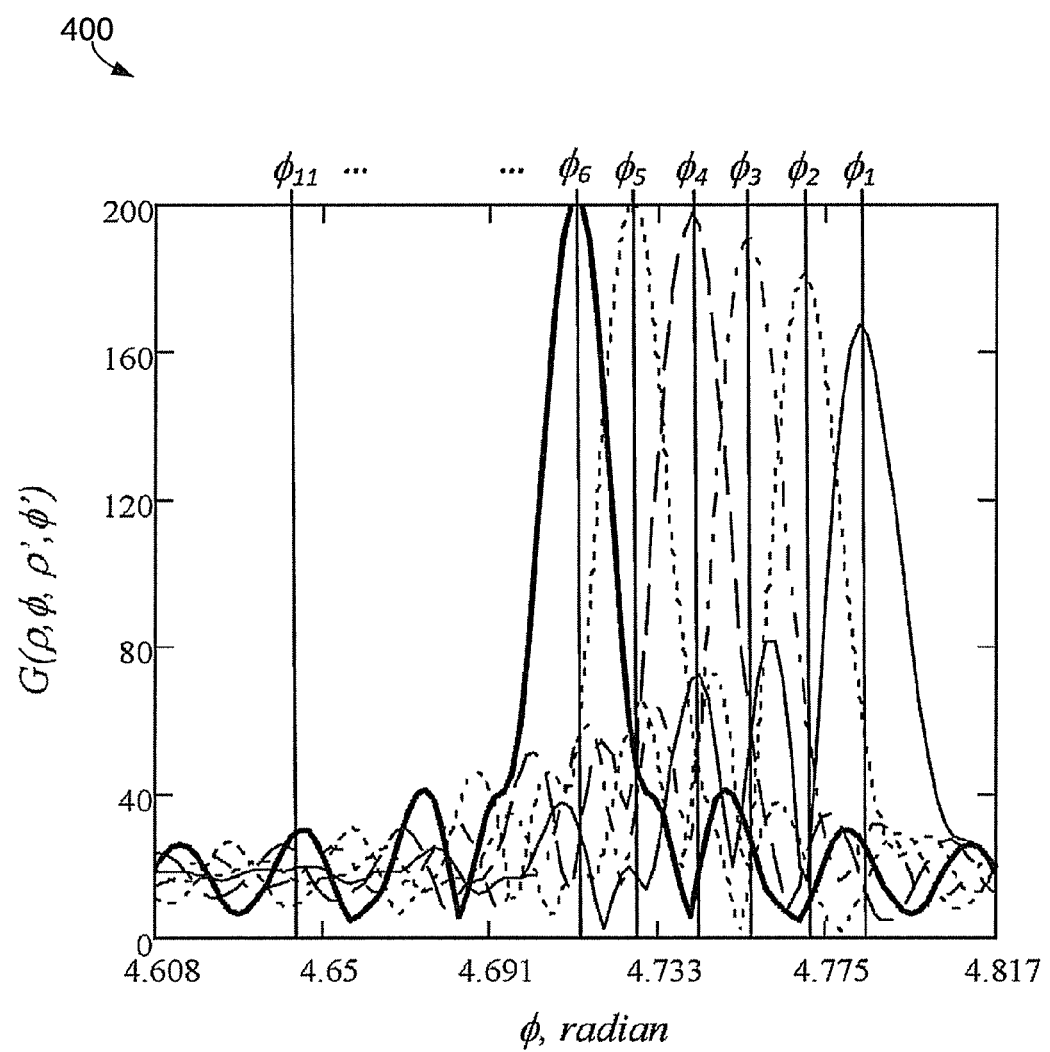
FIG. 4 depicts a graph representing the far field behavior of a parabolic mirror's Green's function for locations of a source point at the support element's centroids of the based functions $b_1$ through $b_6$ shown in FIG. 3.

The behavior of the far field of the Green's function $G(\rho, \phi, \rho_{p'})$ for the source parabolic mirror 330 is depicted on the graph 400 as shown in FIG. 4 for six locations of source point $c_{p'}$, $\rho'=1, \ldots, 6$ of the imaging domain pixel centroids. The angular shift in the maximum of the far field is due to the steering of the main lobe of the radiation due to the source point offset from the mirror focus. The parabolic mirror's 330 Green's function conditions the inverse problem solution by spatially partitioning the field of contrast sources W into distinct beams 306.

Figure 5:
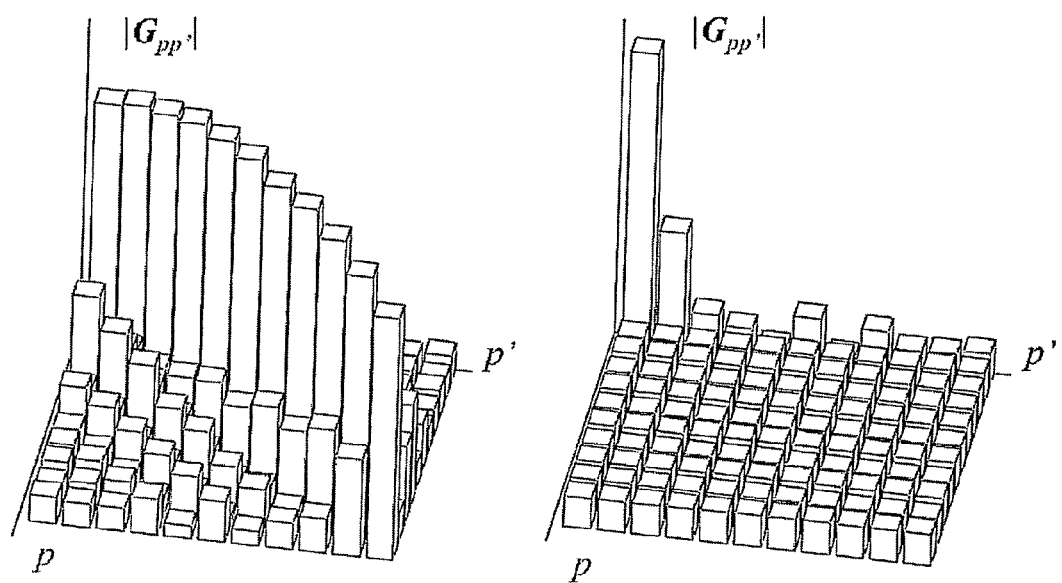
FIG. 5 depicts two 3-dimensional graphs representing the magnitude of inverse problem matrix elements associated with the imaging configuration shown in FIG. 3.

The left sub-plot 500 in FIG. 5 depicts discrete inverse problem matrix G in equation (5) when the scattered field $E(\rho_\rho)-E^i(\rho_\rho)$ is sampled at the points $\rho_\rho=10a(\cos(\phi_\rho)\hat{x}+\sin(\phi_\rho)\hat{y})$, p=1, . . . , P; P=11, coinciding in angular coordinates with the directions $\phi_1, \phi_2, \ldots, \phi_P$ of the corresponding parabolic mirror Green's function beams (see FIG. 4). The separation of the scattered fields from different pixels of the imaging domain produces diagonally-dominant inverse problem matrix G in equation (5). The condition number of the diagonally-dominant (11×11) matrix G shown in the left sub-plot 500 of FIG. 5 is 11.5. Since the matrix equation (5) is well-conditioned, it can be solved directly to find the unknown contrast source coefficients $W_p$, p=1, . . . , P. Upon substitution of thus found contrast source expansion coefficients into equation (7), the total field samples $E_p$ in the imaging domain and subsequently the unknown contrast coefficients $\chi_p$, from equation (8) are obtained. The found values of the real and imaginary parts of the reconstructed contrast are shown in table 600 of FIG. 6 in the fourth and fifth columns, respectively.

For comparison, in the right sub-plot 502 of FIG. 5, the inverse scattering matrix G in equation (5) when the scattered field $E(\rho_\rho)-E^i(\rho_\rho)$ is sampled at observation points situated at the same radial distance of 10a but in the angular directions shifted by 1 rad from the beams of the source parabolic mirror, i.e., $\rho_\rho=10a(\cos(\phi_\rho+1)\hat{x}+\sin(\phi_\rho+1)\hat{y})$, p=1, . . . , P; P=11 is shown. In this example, the scattered fields produced by different pixels (basis functions) of the contrast sources are indistinguishable from each other, which may lead to the classical ill-conditioned formulation of the inverse problem (5). The condition number of the (11×11) matrix G in this case is $5\times10^{10}$. The solution of the linear equations (5) with such matrix followed by evaluations of the field in equation (7) and the contrast in equation (8) yields a highly erroneous solution for which the real and imaginary parts are given in the sixth and seventh columns of table 600 as shown in FIG. 6.

The numerical results of the Veselago lens imaging configuration 700 as shown in FIG. 7, which also allows for a well-conditioned non-iterative solution of the inverse problem, will be described herein after a description of the Veselago lens imaging configuration 700 itself.

An exemplary imaging configuration 700 using a Veselago lens configured to image object 702 is depicted in FIG. 7. The imaging configuration 700 includes transmitting source 722, separation apparatus 724, and receiving apparatus 726.

The transmitting source 722, or source point, is configured to provide an incident field 701 to interrogate or irradiate an image domain, e.g., the object 702. The separation apparatus 724 includes a Veselago lens 730, which is configured (e.g., positioned in relation to the object 702) such that it may spatially separate the scattered field 705 emanating from the image domain, e.g., the object 702, by directing radiated fields 706 produced by the plurality of individualized regions 704 of the image domain (e.g., object 702). Spatially separating the scattered field 705 results in a radiated field 306 corresponding to each of the plurality of individualized regions 704.

The Veselago lens 730 further focuses each radiated field 706 at each of a plurality of observation locations 708 corresponding to each of the plurality of individualized regions 704. For example, individualized region $S_1$ corresponds to observation location $f_1$, individualized region $S_2$ corresponds to observation location $f_2$, individualized region $S_3$ corresponds to observation location $f_3$, etc. In essence, not only does the Veselago lens 730 act as the separation apparatus 724 but it also acts as the focusing apparatus, similar to the focusing apparatus 326 of the parabolic mirror imaging configuration 300 as described herein with reference to FIGS. 3-6.

Although the observations locations 708 as depicted in FIG. 7 appear to be located about the same distance away from each other as each of the individualized regions 704 of the object 702, the observation locations 708 may be located (e.g., spaced) further away from (or closer to) each other than the individualized regions 704 depending on the configuration (e.g., shape, size, etc.) of the Veselago lens 730. For example, the Veselago lens 730 may be shaped so as to spread the radiated fields 706 apart from one another (e.g., further spatially separate) such that the observation locations 708 (e.g., wherein the radiated fields 706 are to be sampled) are separated by a distance that is greater than the distance between individualized regions 704 of the object 702.

The receiving apparatus 726 includes a plurality of antennas. Each of the plurality of antennas is located at the plurality of observation locations 708 and is configured to receive each of the radiated fields 706. Further, although the observation locations 708 as shown are arranged in a grid next to one another, each of the plurality of observation locations 708 is located separately from the other observation locations. In other words, each of the plurality of observation locations 708 is located a distance away from the other observation locations 708.

In at least another embodiment, the receiving apparatus 726 includes at least one antenna (e.g., one antenna, two antennas, two or more antennas, five or more antennas, twenty or less antennas, fifty or less antennas, etc.) that is positionable in each or many of the plurality of observation locations 708 to, e.g., receive each radiated field 706. In other words, the receiving apparatus 726 may include fewer antennas (e.g., a factor of the number of observation locations 708) than observation locations 708. The antennas may be movable such that each radiated field 706 may be sampled at each observation location 708.

In this example, the desired focusing properties of the Green's function radiation are inherent to the mathematical model of the Veselago lens 730. Due to the effect of negative refraction, the lens 730 produces radiated fields 706 from the scattered field 705 at each of the observation locations 708 $f_1, \ldots, f_P$ corresponding with each of the individualized regions 704 of imaging domain basis function centroids $c_1, \ldots, c_P$ as shown in FIG. 7.

For example, the material properties of the Veselago lens 730 selected for this numerical example are $\in_1 = -4.0$, $\mu_1 = -3.999$ and the background medium $\in_b = 4.0$, $\mu_b = 4.0$. Further, for example, the boundaries of the Veselago lens 730 are located at y=−0.75 m and y=−0.25 m. The time-harmonic cyclic frequency of the lens 730 is $2\pi \cdot 6.777$ GHz. The imaging domain (e.g., the object 702) of dimensions L=T=3.5λ=0.155 m is discretized with P=7·7=49 square basis function supporting elements each with area $S_p = \Delta L \Delta T = (0.022 \text{ m})^2$, $p=1, \ldots, P$. The incident field 701 interrogating the imaging domain 702 is produced by the filament of z-directed current located at the source point 722 $\rho_0 = 0.265 \text{ m}(\hat{x}+\hat{y})$.

Figure 8:
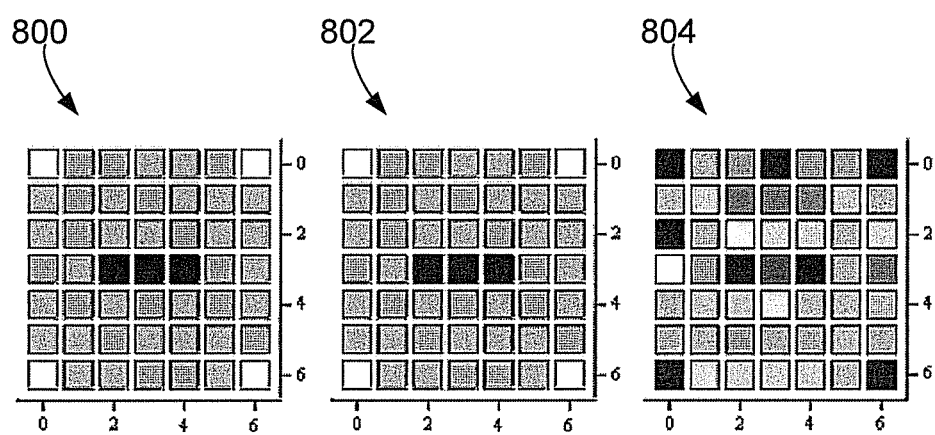
FIG. 8 depicts three sub-plots representing an image domain and reconstruction of the image domain using the imaging configuration of FIG. 7.

The left sub-plot 800 shown in FIG. 8 depicts the spatial distribution of the contrast function χ subjected to image reconstruction where the black elements correspond to contrast value χ=−2.0, grey elements to χ=−1.0, and white elements to χ=0.0. In the parabolic mirror imaging configuration 300, the observation points in equation (4) at which the scattered field is sampled are taken to coincide with the lens focal points $f_p = c_p - 2d\hat{y}$, where $c_p$ is the centroid of the $b_p$th imaging domain basis function support element, and d is the thickness of the lens. In this Veselago lens imaging configuration 700, the system of equation (5) is well-conditioned. The contrast source expansion coefficients $W_p$, $p=1, \ldots, P$ found through direct inversion of matrix G and subsequently substituted into equations (7) and (8) yield the image reconstruction with the maximum relative error not exceeding 4.5% as shown in the middle sub-plot 802 in FIG. 8.

Positioning the observation points off the corresponding focus points at locations $\rho_p = f_p - \hat{y} 0.265$ m, however, leads to the classical ill-conditioning of the system as shown in equation (5). The image reconstructed with the scattered field sampled at these observation points is depicted in the right sub-plot 804 in FIG. 8.

Further, alternative approaches to formation of desired focusing properties of the Green's function are possible. For example, one of such approaches is through construction of an appropriate phased-antenna array as depicted in FIG. 9.

An exemplary imaging configuration 900 using a phased-antenna array configured to image object 902 is depicted in FIG. 9. The imaging configuration 900 includes transmitting source 922, separation apparatus 924, and receiving apparatus (not shown).

The transmitting source 922, or source point, is configured to provide an incident field 901 to interrogate or irradiate an image domain, e.g., the object 902. The separation apparatus 924 includes a phased-antenna array 930, which is configured (e.g., positioned in relation to the object 902) such that it may spatially separate the scattered field 905 emanating from the image domain, e.g., the object 902, by directing radiated fields 906 produced by the plurality of individualized regions 904 of the image domain (e.g., object 902). Spatially separating the scattered field 905 results in a radiated field 906 corresponding to each of the plurality of individualized regions 904.

The phased-antenna array 930 includes a plurality of phased-antennas 932. One or more of the plurality of phased-antennas may be configured to receive the scattered field 905 emanating from corresponding individualized regions 904 of the image domain and to direct, e.g., transmit or reflect, such radiated fields 906 in a particular direction, e.g., at a particular angle 908, corresponding to the particular individualized region 904. For example, individualized region $S_1$ corresponds to angle $P_1$, individualized region $S_2$ corresponds to angle $P_2$, individualized region $S_3$ corresponds to angle $P_3$, etc. As depicted in FIG. 9, individualized region $S_7$ corresponds to angle $P_7$ and individualized region $S_{22}$ corresponds to angle $P_{22}$. In at least one embodiment, a group of antennas (e.g., two or more antennas) may correspond to one individualized region (e.g., the group may correspond to one pixel of a reconstructed image where the one pixel corresponds to the one individualized region).

The phased-antenna array 930 may be spherical (e.g., the antennas may be arranged on a surface conforming to a sphere or at least a portion of a sphere), planar (e.g., the antennas may lie in a plane), and/or any other shape or size configured to spatially separate the scattered field 905.

Different designs of the phased antenna array elements can be also utilized in construction of the desirable array. Further, the phased antennas may be either passive (e.g., not requiring additional power), active (e.g., requiring additional power), or of various design. Still further, assignment of phased-antenna array elements to a pixel may vary per specific beam forming algorithm and both phase shifts and gain factors of the phased-antenna array elements may be adjusted per one or more algorithms.

Further, although not shown, the imaging configuration 900 may include receiving apparatus. Such receiving apparatus may be similar to the other receiving apparatus described herein, e.g., with reference to FIGS. 1 & 3 but may be configured to receive (e.g., sample) the radiated fields 906 directed at the particular angles 908. Further, such received radiated fields 906 may be used in a similar manner as described herein to reconstruct an image of the object 902.

All references cited herein are incorporated in their entirety as if each were incorporated separately. This present disclosure has been described with reference to illustrative embodiments and is not meant to be construed in a limiting sense. Various modifications of the illustrative embodiments, as well as additional embodiments, will be apparent to persons skilled in the art upon reference to this description.

What is claimed is:

1. A method for use in imaging an imaging domain comprising:
   providing an incident field to interrogate an image domain resulting in a scattered field emanating from the image domain;
   spatially separating the scattered field emanating from the image domain by directing radiated fields produced by a plurality of individualized regions of the image domain, wherein spatially separating the scattered field comprises using separation apparatus to direct the radiated fields produced by the plurality of individualized regions of the image domain, and further wherein spatially separating the scattered field results in a radiated field corresponding to each of the plurality of individualized regions of the image domain;
   sampling the radiated fields at each of a plurality of observation locations corresponding to each of the plurality of individualized regions of the image domain; and
   reconstructing an image corresponding to the image domain based on the sampled radiated fields.

2. The method of claim 1, wherein spatially separating the scattered field comprises directing at least one of the radiated fields in a different direction than the other radiated fields.

3. The method of claim 2, wherein directing at least one of the radiated fields in a different direction than the other radiated fields comprises directing at least one of the radiated fields at a different angle than the other radiated fields.

4. The method of claim 1, wherein spatially separating the scattered field comprises directing each of the radiated fields in a different direction than each of the other radiated fields.

5. The method of claim 1, wherein spatially separating the scattered field comprises directing at least one of the radiated fields to a different observation location of the plurality of observation locations than the other observation locations of the plurality of observation locations at which the other radiated fields are directed.

6. The method of claim 1, wherein spatially separating the scattered field comprises directing each of the radiated fields to a different observation location of the plurality of observation locations than the other observation locations of the plurality of observation locations at which the other radiated fields are directed.

7. The method of claim 1, wherein each of the plurality of observation locations is located a distance away from the other observation locations of the plurality of observation locations.

8. The method of claim 1, wherein the separation apparatus comprises a Veselago lens.

9. The method of claim 1, wherein the separation apparatus comprises a phased-antenna array.

10. The method of claim 1, wherein the separation apparatus comprises a parabolic mirror.

11. The method of claim 1, wherein reconstructing an image corresponding to the image domain based on the sampled radiated fields comprises using a well-conditioned diagonally-dominant matrix representative of a linear system of linear equations each corresponding to one of the plurality of observation locations.

12. A method for use in imaging an imaging domain comprising:
    providing an incident field to interrogate an image domain resulting in a scattered field emanating from the image domain;
    spatially separating the scattered field emanating from the image domain by directing radiated fields produced by a plurality of individualized regions of the image domain, wherein spatially separating the scattered field results in a radiated field corresponding to each of the plurality of individualized regions of the image domain;
    sampling the radiated fields at each of a plurality of observation locations corresponding to each of the plurality of individualized regions of the image domain; and
    reconstructing an image corresponding to the image domain based on the sampled radiated fields, wherein the plurality of observation locations correspond to a plurality of focal points, and wherein the method further comprises focusing each of the radiated fields at one of the plurality of focal points.

13. The method of claim 12, wherein spatially separating the scattered field emanating from the image domain comprises using separation apparatus to direct the radiated fields produced by the plurality of individualized regions of the image domain.

14. A system for use in imaging an imaging domain comprising:
    a transmitting source to provide an incident field, wherein the incident field when interrogating an image domain results in a scattered field emanating from the image domain;
    separation apparatus configured to spatially separate a scattered field emanating from the image domain upon being interrogated by the incident field by directing radiated fields produced by a plurality of individualized regions of the image domain resulting in a radiated field corresponding to each of the plurality of individualized regions of the image domain;
    receiving apparatus configured to receive the radiated fields at each of a plurality of observation locations corresponding to each of the plurality of individualized regions of the image domain; and
    processing apparatus configured to reconstruct an image corresponding to the image domain based on the received radiated fields.

15. The system of claim 14, wherein the separation apparatus is further configured to direct at least one of the radiated fields in a different direction than the other radiated fields.

16. The system of claim 15, wherein the at least one of the radiated fields directed by the separation apparatus are directed at a different angle than the other radiated fields.

17. The system of claim 14, wherein the separation apparatus is further configured to direct each of the radiated fields in a different direction than the other radiated fields.

18. The system of claim 14, wherein the separation apparatus is further configured to direct at least one of the radiated fields to a different observation location of the plurality of observation locations than other observation locations of the plurality of observation locations at which the other radiated fields are directed.

19. The system of claim 14, wherein the separation apparatus is further configured to direct each of the radiated fields to a different observation location of the plurality of observations than other observation locations of the plurality of observation locations at which the other radiated fields are directed.

20. The system of claim 14, wherein each of the plurality of observation locations are located a distance away from the other observation locations of the plurality of observation locations.

21. The system of claim 14, wherein the separation apparatus comprises a Veselago lens.

22. The system of claim 14, wherein the separation apparatus comprises a parabolic mirror.

23. The system of claim 14, wherein the separation apparatus comprises a phased-antenna array.

24. The system of claim 14, wherein the plurality of observation locations correspond to a plurality of focal points, and wherein the separation apparatus comprises focusing apparatus configured to focus each radiated field at a different focal point of the plurality of focal points than other focal points of the plurality of focal points at which the other radiated fields are focused.

25. The system of claim 24, wherein the focusing apparatus comprises a parabolic mirror for each radiated field.

26. The system of claim 14, wherein the processing apparatus is operable to reconstruct an image corresponding to the image domain based on the received radiated fields using a well-conditioned diagonally-dominant matrix representative of a linear system of linear equations each corresponding to one of the plurality of observation locations.

* * * * *